(12) United States Patent
Lim et al.

(10) Patent No.: US 9,433,528 B2
(45) Date of Patent: Sep. 6, 2016

(54) INTRAVASCULAR HEAT EXCHANGE CATHETER WITH RIB CAGE-LIKE COOLANT PATH

(71) Applicant: Zoll Circulation, Inc., Sunnyvale, CA (US)

(72) Inventors: Alex L. Lim, Santa Clara, CA (US); Masouneh Mafi, Mountain View, CA (US); Venkata Vishnu Gurukula, Mountain View, CA (US); Richard A. Helkowski, Redwood City, CA (US)

(73) Assignee: Zoll Circulation, Inc., San Jose, CA (US)

( * ) Notice: Subject to any disclaimer, the term of this patent is extended or adjusted under 35 U.S.C. 154(b) by 598 days.

(21) Appl. No.: 13/675,241

(22) Filed: Nov. 13, 2012

(65) Prior Publication Data

US 2014/0094883 A1    Apr. 3, 2014

Related U.S. Application Data

(60) Provisional application No. 61/707,146, filed on Sep. 28, 2012.

(51) Int. Cl.
*A61F 7/12* (2006.01)
*A61F 7/02* (2006.01)

(52) U.S. Cl.
CPC ............. *A61F 7/12* (2013.01); *A61F 2007/126* (2013.01)

(58) Field of Classification Search
CPC .................................................. A61F 2007/126
USPC ............ 607/104, 96, 99, 113, 105; 165/142, 165/177, 45
See application file for complete search history.

(56) References Cited

U.S. PATENT DOCUMENTS

| | | |
|---|---|---|
| 1,459,112 A | 6/1923 | Mehl |
| 1,857,031 A | 5/1932 | Schaffer |
| 2,663,030 A | 12/1953 | Dahlberg |
| 2,673,987 A | 4/1954 | Upshaw et al. |
| 3,225,191 A | 12/1965 | Calhoun |
| 3,369,549 A | 2/1968 | Armao |
| 3,425,419 A | 2/1969 | Dato |
| 3,504,674 A | 4/1970 | Swenson |
| 3,726,269 A | 4/1973 | Webster, Jr. |
| 3,744,555 A | 7/1973 | Fletcher et al. |
| 3,751,077 A | 8/1973 | Hiszpanski |

(Continued)

FOREIGN PATENT DOCUMENTS

| | | |
|---|---|---|
| DE | 19531935 | 2/1997 |
| GB | 2040169 | 8/1980 |

(Continued)

OTHER PUBLICATIONS

F.W. Behmann, E Bontke, "Die Regelung der Warmebildung bei künstlicher Hypothermie", Pflügers Archie, Bd. .266, S. 408-421 (1958).

(Continued)

*Primary Examiner* — Kaitlyn Smith
*Assistant Examiner* — Yasamin Ekrami
(74) *Attorney, Agent, or Firm* — John L. Rogitz

(57) ABSTRACT

An intravascular heat exchange catheter has serpentine-like supply and return conduits circulating working fluid with a heat exchange system to warm or cool a patient in which the catheter is intubated.

15 Claims, 2 Drawing Sheets

(56) References Cited

U.S. PATENT DOCUMENTS

| | | |
|---|---|---|
| 3,937,224 A | 2/1976 | Uecker |
| 3,945,063 A | 3/1976 | Matsuura |
| 4,038,519 A | 7/1977 | Foucras |
| 4,065,264 A | 12/1977 | Lewin |
| 4,103,511 A | 8/1978 | Kress et al. |
| 4,126,132 A | 11/1978 | Portner et al. |
| 4,153,048 A | 5/1979 | Magrini |
| 4,173,228 A | 11/1979 | Van Steenwyk et al. |
| 4,181,132 A | 1/1980 | Parks |
| 4,298,006 A | 11/1981 | Parks |
| 4,459,468 A | 7/1984 | Bailey |
| 4,532,414 A | 7/1985 | Shah et al. |
| 4,554,793 A | 11/1985 | Harding, Jr. |
| 4,581,017 A | 4/1986 | Sahota |
| 4,638,436 A | 1/1987 | Badger et al. |
| 4,653,987 A | 3/1987 | Tsuji et al. |
| 4,661,094 A | 4/1987 | Simpson |
| 4,665,391 A | 5/1987 | Spani |
| 4,672,962 A | 6/1987 | Hershenson |
| 4,754,752 A | 7/1988 | Ginsburg et al. |
| 4,787,388 A | 11/1988 | Hofmann |
| 4,813,855 A | 3/1989 | Leveen et al. |
| 4,849,196 A | 7/1989 | Yamada et al. |
| 4,852,567 A | 8/1989 | Sinofsky |
| 4,860,744 A | 8/1989 | Johnson et al. |
| 4,906,237 A | 3/1990 | Johansson et al. |
| 4,941,475 A | 7/1990 | Williams et al. |
| 5,092,841 A | 3/1992 | Spears |
| 5,103,360 A | 4/1992 | Maeda |
| 5,106,360 A | 4/1992 | Ishiwara et al. |
| 5,192,274 A | 3/1993 | Bierman |
| 5,195,965 A | 3/1993 | Shantha |
| 5,211,631 A | 5/1993 | Sheaff |
| 5,269,758 A | 12/1993 | Taheri |
| 5,281,215 A | 1/1994 | Milder |
| 5,304,214 A | 4/1994 | DeFord et al. |
| 5,342,301 A | 8/1994 | Saab |
| 5,344,436 A | 9/1994 | Fontenot et al. |
| 5,370,675 A | 12/1994 | Edwards et al. |
| 5,383,856 A | 1/1995 | Bersin |
| 5,403,281 A | 4/1995 | O'Neill et al. |
| 5,433,740 A | 7/1995 | Yamaguchi |
| 5,437,673 A | 8/1995 | Baust et al. |
| 5,458,639 A | 10/1995 | Tsukashima et al. |
| 5,486,207 A | 1/1996 | Mahawili |
| 5,486,208 A | 1/1996 | Ginsburg |
| 5,507,792 A | 4/1996 | Mason et al. |
| 5,531,714 A | 7/1996 | Dahn et al. |
| 5,531,776 A | 7/1996 | Ward et al. |
| 5,624,392 A | 4/1997 | Saab |
| 5,634,907 A | 6/1997 | Rani et al. |
| 5,676,670 A | 10/1997 | Kim |
| 5,701,905 A | 12/1997 | Esch |
| 5,709,564 A | 1/1998 | Yamada et al. |
| 5,709,654 A | 1/1998 | Klatz et al. |
| 5,716,386 A | 2/1998 | Ward et al. |
| 5,730,720 A | 3/1998 | Sites et al. |
| 5,733,319 A | 3/1998 | Neilson et al. |
| 5,737,782 A | 4/1998 | Matsuura et al. |
| 5,776,079 A | 7/1998 | Cope et al. |
| 5,788,647 A | 8/1998 | Eggers |
| 5,837,003 A | 11/1998 | Ginsburg |
| 5,862,675 A | 1/1999 | Scaringe et al. |
| 5,895,418 A | 4/1999 | Saringer |
| 5,908,407 A | 6/1999 | Frazee et al. |
| 5,957,963 A | 9/1999 | Dobak, III |
| 5,980,561 A | 11/1999 | Kolen et al. |
| 6,019,783 A | 2/2000 | Philips et al. |
| 6,042,559 A | 3/2000 | Dobak, III |
| 6,051,019 A | 4/2000 | Dobak, III |
| 6,059,825 A * | 5/2000 | Hobbs et al. ............... 623/1.18 |
| 6,096,068 A | 8/2000 | Dobak, III et al. |
| 6,106,522 A * | 8/2000 | Fleischman et al. ............ 606/41 |
| 6,110,139 A | 8/2000 | Loubser |
| 6,117,065 A | 9/2000 | Hastings et al. |
| 6,117,105 A | 9/2000 | Bresnaham et al. |
| 6,124,452 A | 9/2000 | Di Magno |
| 6,126,684 A | 10/2000 | Gobin et al. |
| 6,146,141 A | 11/2000 | Schumann |
| 6,146,411 A | 11/2000 | Noda et al. |
| 6,148,634 A | 11/2000 | Sherwood |
| 6,149,670 A | 11/2000 | Worthen et al. |
| 6,149,677 A | 11/2000 | Dobak, III |
| 6,231,594 B1 | 5/2001 | Dae |
| 6,261,312 B1 | 7/2001 | Dobak, III et al. |
| 6,280,441 B1 * | 8/2001 | Ryan ............................... 606/45 |
| 6,283,940 B1 | 9/2001 | Mulholland |
| 6,299,599 B1 | 10/2001 | Pham et al. |
| 6,308,090 B1 * | 10/2001 | Tu et al. ......................... 600/374 |
| 6,322,559 B1 * | 11/2001 | Daulton et al. ................. 606/41 |
| 6,338,727 B1 | 1/2002 | Noda et al. |
| 6,383,144 B1 | 5/2002 | Mooney et al. |
| 6,409,747 B1 | 6/2002 | Gobin et al. |
| 6,416,533 B1 | 7/2002 | Gobin et al. |
| 6,428,563 B1 | 8/2002 | Keller |
| 6,450,990 B1 | 9/2002 | Walker et al. |
| 6,451,045 B1 * | 9/2002 | Walker et al. ................. 607/105 |
| 6,464,716 B1 | 10/2002 | Dobak, III et al. |
| 6,527,798 B2 | 3/2003 | Ginsburg et al. |
| 6,530,946 B1 | 3/2003 | Noda et al. |
| 6,544,282 B1 | 4/2003 | Dae et al. |
| 6,551,309 B1 | 4/2003 | Le Pivert |
| 6,554,791 B1 | 4/2003 | Cartledge et al. |
| 6,589,271 B1 | 7/2003 | Tzeng et al. |
| 6,605,106 B2 | 8/2003 | Schwartz |
| 6,610,083 B2 | 8/2003 | Keller et al. |
| 6,620,187 B2 | 9/2003 | Carson et al. |
| 6,620,188 B1 | 9/2003 | Ginsburg et al. |
| 6,624,679 B2 | 9/2003 | Tomaiuolo et al. |
| 6,635,079 B2 | 10/2003 | Unsworth et al. |
| 6,673,042 B1 * | 1/2004 | Samson et al. ................. 604/104 |
| 6,679,906 B2 | 1/2004 | Hammack et al. |
| 6,685,733 B1 | 2/2004 | Dae et al. |
| 6,706,060 B2 | 3/2004 | Tzeng et al. |
| 6,716,188 B2 | 4/2004 | Noda et al. |
| 6,719,723 B2 | 4/2004 | Werneth |
| 6,719,779 B2 | 4/2004 | Daoud |
| 6,726,653 B2 | 4/2004 | Noda et al. |
| 6,740,109 B2 | 5/2004 | Dobak, III |
| 6,746,474 B2 * | 6/2004 | Saadat .......................... 607/105 |
| 6,799,342 B1 | 10/2004 | Jarmon |
| 6,843,800 B1 | 1/2005 | Dobak, III |
| 6,887,263 B2 | 5/2005 | Bleam et al. |
| 6,893,419 B2 | 5/2005 | Noda et al. |
| 6,969,399 B2 | 11/2005 | Schock et al. |
| 7,156,843 B2 * | 1/2007 | Skarda ............................. 606/41 |
| 7,510,569 B2 | 3/2009 | Dae et al. |
| 7,666,215 B2 | 2/2010 | Callister et al. |
| 7,686,070 B2 * | 3/2010 | Chu et al. .................. 165/109.1 |
| 7,822,485 B2 | 10/2010 | Collins |
| 7,846,193 B2 | 12/2010 | Dae et al. |
| 7,857,781 B2 | 12/2010 | Noda et al. |
| 8,105,262 B2 | 1/2012 | Noda et al. |
| 8,105,263 B2 | 1/2012 | Noda et al. |
| 8,105,264 B2 | 1/2012 | Noda et al. |
| 8,109,894 B2 | 2/2012 | Noda et al. |
| 2001/0031946 A1 | 10/2001 | Walker et al. |
| 2001/0047196 A1 | 11/2001 | Ginsburg et al. |
| 2002/0013569 A1 | 1/2002 | Sterman et al. |
| 2002/0022823 A1 | 2/2002 | Luo et al. |
| 2002/0145525 A1 | 10/2002 | Friedman et al. |
| 2002/0147445 A1 * | 10/2002 | Farley et al. .................... 606/33 |
| 2002/0183692 A1 | 12/2002 | Callister |
| 2002/0198579 A1 | 12/2002 | Khanna |
| 2003/0023288 A1 * | 1/2003 | Magers .......................... 607/106 |
| 2003/0139750 A1 | 7/2003 | Shinozuka et al. ............ 606/113 |
| 2003/0176902 A1 * | 9/2003 | Gunn et al. .................... 607/104 |
| 2003/0236496 A1 | 12/2003 | Samson et al. |
| 2004/0015221 A1 * | 1/2004 | Kuzma .......................... 607/116 |
| 2004/0044387 A1 * | 3/2004 | Pompa et al. ................. 607/105 |
| 2004/0089058 A1 | 5/2004 | De Haan et al. |
| 2004/0102825 A1 | 5/2004 | Daoud |
| 2004/0210231 A1 | 10/2004 | Boucher et al. |
| 2005/0010273 A1 * | 1/2005 | Walker et al. ................. 607/105 |

(56) References Cited

U.S. PATENT DOCUMENTS

| | | |
|---|---|---|
| 2005/0156744 A1 | 7/2005 | Pires |
| 2006/0095104 A1* | 5/2006 | Magers et al. ............... 607/105 |
| 2006/0185828 A1* | 8/2006 | Takehara et al. ........ 165/104.26 |
| 2007/0007640 A1 | 1/2007 | Harnden et al. |
| 2007/0076401 A1 | 4/2007 | Carrez et al. |
| 2008/0154297 A1* | 6/2008 | Lee et al. .................... 606/190 |
| 2008/0262584 A1* | 10/2008 | Bottomley et al. .......... 607/119 |
| 2009/0018534 A1* | 1/2009 | Taimisto et al. ............... 606/33 |
| 2009/0056927 A1* | 3/2009 | Zobel et al. .................. 165/180 |
| 2009/0062837 A1* | 3/2009 | Gasche et al. ............... 606/197 |
| 2009/0247963 A1* | 10/2009 | Bleam et al. ................. 604/246 |
| 2011/0270368 A1 | 11/2011 | Ginsburg et al. |

FOREIGN PATENT DOCUMENTS

| | | |
|---|---|---|
| GB | 1183185 | 2/1985 |
| GB | 2212262 | 7/1989 |
| GB | 2383828 | 7/2003 |
| JP | 09-215754 | 8/1997 |
| JP | 10-0127777 | 5/1998 |
| JP | 10-305103 | 11/1998 |
| WO | 9001682 | 2/1990 |
| WO | 9304727 | 3/1993 |
| WO | 9400177 | 1/1994 |
| WO | 9401177 | 1/1994 |
| WO | 9725011 | 7/1997 |
| WO | 9824491 | 6/1998 |
| WO | 9840017 | 9/1998 |
| WO | 0010494 | 3/2000 |
| WO | 0113809 | 3/2001 |
| WO | 0164146 | 9/2001 |
| WO | 0176517 | 10/2001 |
| WO | 0183001 | 11/2001 |

OTHER PUBLICATIONS

F.W. Behmann, E. Bontke, "Intravasale Kühlung", Pflügers Archie, Bd. 263, S. 145-165 (1956).

Wilhelm Behringer, Stephan Prueckner, Rainer Kenter, Samuel A. Tisherman, Ann Radovsky, Robert Clark, S. William Stezoski, Heremy Henchir, Edwin Klein, Peter Safar, "Rapid Hypothermic Aortic Flush Can Achieve Survival without Brain Damage after 30 Minutes Cardiac Arrest in Dogs", anesthesiology, V. 93, No. 6, Dec. 2000.

Dorraine Day Watts, Arthur Trask, Karen Soeken, Philip Predue, Sheilah Dols, Christopher Kaufman; "Hypothermic Coagulopathy in trauma: Effect of Varying levels of Hypothermia on Enzyme Speed, Platelet Function, and Fibrinolytic Activity". The Journal of Trauma: Injury, Infection, and Critical Care, vol. 44, No. 5 (1998).

* cited by examiner

INTRAVASCULAR HEAT EXCHANGE CATHETER WITH RIB CAGE-LIKE COOLANT PATH

I. FIELD OF THE INVENTION

The present application relates generally to patient temperature control systems.

II. BACKGROUND OF THE INVENTION

It has been discovered that the medical outcome for a patient suffering from severe brain trauma or from ischemia caused by stroke or heart attack or cardiac arrest is improved if the patient is cooled below normal body temperature (37° C.). Furthermore, it is also accepted that for such patients, it is important to prevent hyperthermia (fever) even if it is decided not to induce hypothermia. Moreover, in certain applications such as post-CABG surgery, skin graft surgery, and the like, it might be desirable to rewarm a hypothermic patient.

As recognized by the present application, the above-mentioned advantages in regulating temperature can be realized by cooling or heating the patient's entire body using a closed loop heat exchange catheter placed in the patient's venous system and circulating a working fluid such as saline through the catheter, heating or cooling the working fluid as appropriate in an external heat exchanger that is connected to the catheter. The following U.S. patents, all of which are incorporated herein by reference, disclose various intravascular catheters/systems/methods for such purposes: U.S. Pat. Nos. 6,881,551 and 6,585,692 (tri-lobe catheter), U.S. Pat. Nos. 6,551,349 and 6,554,797 (metal catheter with bellows), U.S. Pat. Nos. 6,749,625 and 6,796,995 (catheters with non-straight, non-helical heat exchange elements), U.S. Pat. Nos. 6,126,684, 6,299,599, 6,368,304, and 6,338,727 (catheters with multiple heat exchange balloons), U.S. Pat. Nos. 6,146,411, 6,019,783, 6,581,403, 7,287,398, and 5,837,003 (heat exchange systems for catheter), U.S. Pat. No. 7,857,781 (various heat exchange catheters).

SUMMARY OF THE INVENTION

A catheter includes a heat exchange supply conduit configured to supply working fluid received from a source of working fluid to a distal location, and a heat exchange return conduit communicating with the supply conduit at the distal location and configured to return working fluid to the source. At least a portion of the supply conduit and/or at least a portion of the return conduit is configured in a serpentine configuration when working fluid flows therethrough.

In example embodiments, at least a portion of the supply conduit and at least a portion of the return conduit are configured in a serpentine configuration when working fluid flow therethrough. Furthermore, serpentine portions of the supply conduit establish axially longer segments and axially shorter segments and serpentine portions of the return conduit establish axially longer segments and axially shorter segments. At least one axially shorter segment of the return conduit is bordered by and axially between transverse legs of axially longer segment of the supply conduit and at least one axially shorter segment of the supply conduit is bordered by and axially between transverse legs of an axially longer segment of the return conduit.

As discussed in one example below, when the conduits are inflated with working fluid, a proximal-most transverse segment of the supply conduit ends at a first distally-extending axially-oriented segment, which merges at a distal end with a second transverse segment, which in turn merges at an opposite end of the second transverse segment with another distally-extending axially-oriented segment. Likewise, when the conduits are inflated with working fluid, a distal-most transverse segment of the return conduit ends at a first proximally-extending axially-oriented segment, which merges at a proximal end with a second transverse segment, which in turn merges at an opposite end of the second transverse segment with another proximally-extending axially-oriented segment.

In non-limiting examples, in each conduit, lengths of the axially-oriented segments sequentially alternate between a short length and a long length, while in contrast each transverse segment has substantially the same length as the other transverse segments. Additionally, a long axially-oriented segment of the supply conduit axially spans a short axially-oriented segment of the return conduit, and likewise a long axially-oriented segment of the return conduit axially spans a short axially-oriented segment of the supply conduit. Short axially-oriented segments of the conduits may be substantially straight and parallel to a long axis of the catheter, while long axially-oriented segments the conduits can be concave.

In another aspect, a catheter includes a heat exchange supply conduit configured to supply working fluid received from a source of working fluid to a distal location. A heat exchange return conduit communicates with the supply conduit at the distal location and is configured to return working fluid to the source. At least a portion of the supply conduit and at least a portion of the return conduit are configured in a serpentine configuration when working fluid flow therethrough. Serpentine portions of the supply conduit establish axially longer segments and axially shorter segments and serpentine portions of the return conduit establish axially longer segments and axially shorter segments. At least one axially shorter segment of the return conduit is bordered by and spaced axially between transverse legs of an axially longer segment of the supply conduit and at least one axially shorter segment of the supply conduit is bordered by and axially between transverse legs of an axially longer segment of the return conduit.

In another aspect, an intravascular heat exchange catheter has serpentine-like supply and return conduits circulating working fluid with a heat exchange system to warm or cool a patient in which the catheter is intubated.

The details of the present invention, both as to its structure and operation, can best be understood in reference to the accompanying drawings, in which like reference numerals refer to like parts, and in which:

DETAILED DESCRIPTION OF THE PREFERRED EMBODIMENT

Figure 1:
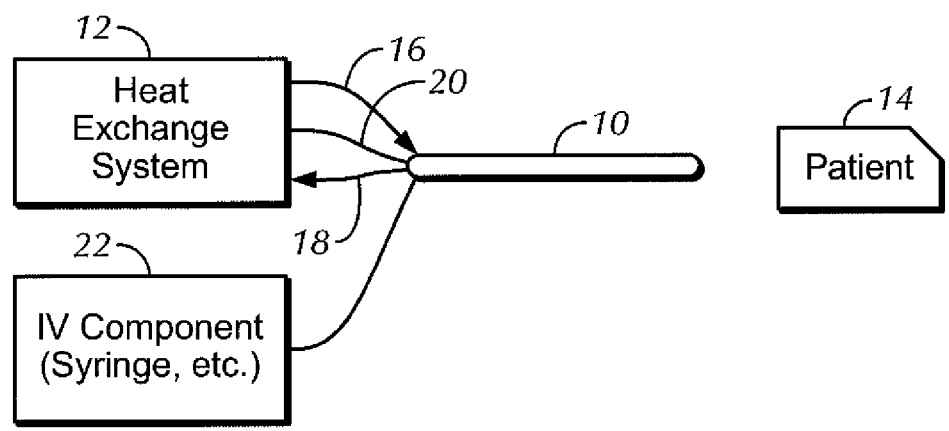
FIG. 1 is a schematic diagram showing an example catheter engaged with an example heat exchange system.

Referring initially to FIG. 1, an intravascular temperature management catheter 10 is in fluid communication with a catheter temperature control system 12 that includes a processor executing logic that in some non-limiting examples is in accordance with disclosure in the above-referenced system patents to control the temperature of working fluid circulating through the catheter 10 in accordance with a treatment paradigm responsive to patient core temperature feedback signals. In accordance with present principles, the catheter 10 can be used to induce therapeutic hypothermia in a patient 14 using the catheter, in which coolant such as but not limited to saline circulates in a closed loop, such that no coolant enters the body. Such treatment may be indicated for stroke, cardiac arrest (post-resuscitation), acute myocardial infarction, spinal injury, and traumatic brain injury. The catheter 10 can also be used to warm a patient, e.g., after bypass surgery or burn treatment, and to combat hyperthermia in, e.g., patient suffering from subarachnoid hemorrhage or intracerebral hemorrhage.

As shown, working fluid such a refrigerant may be circulated between the heat exchange system 12 and catheter 10 through supply and return lines 16, 18 that connect to the proximal end of the catheter 10 as shown. Note that as used herein, "proximal" and "distal" in reference to the catheter are relative to the system 12. A patient temperature signal from a catheter-borne temperature sensor may be provided to the system 12 through an electrical line 20 or wirelessly if desired. Alternatively, a patient temperature signal may be provided to the system 12 from a separate esophageal probe or rectal probe or tympanic sensor or bladder probe or other temperature probe that measures the temperature of the patient 14.

The catheter 10, in addition to interior supply and return lumens through which the working fluid is circulated, may also have one or more infusion lumens connectable to an IV component 22 such as a syringe or IV bag for infusing medicaments into the patient, or an instrument such as an oxygen or pressure monitor for monitoring patient parameters, etc.

The catheter 10 can be positioned typically in the vasculature of the patient 14 and more preferably in the venous system of the patient 14 such as in the inferior vena cava through a groin insertion point or the superior vena cava through a neck (jugular or subclavian) insertion point.

Figure 2:
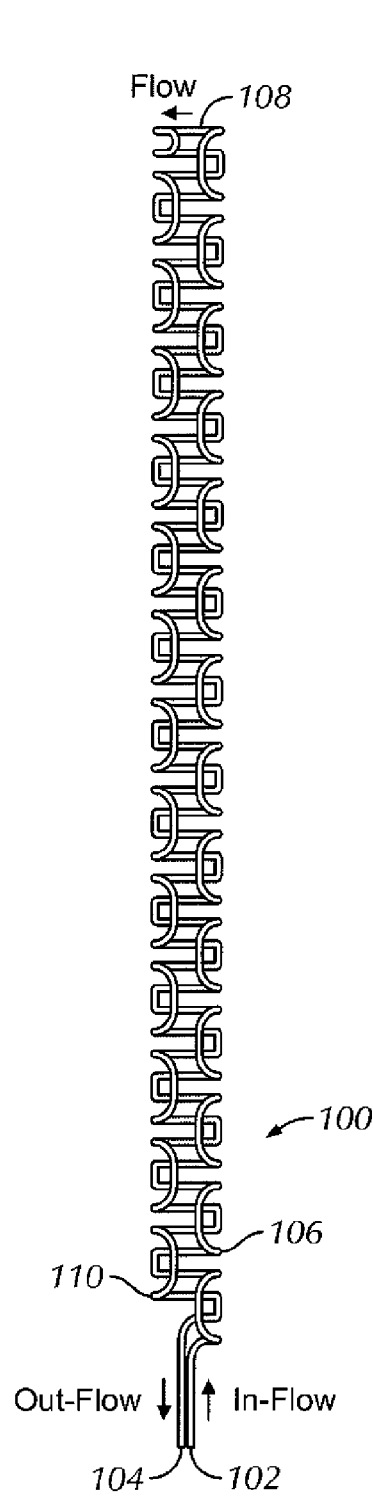
FIG. 2 is a perspective view of the heat exchange region showing only the coolant supply and return lumens and omitting infusion lumens for clarity.
Figure 3:
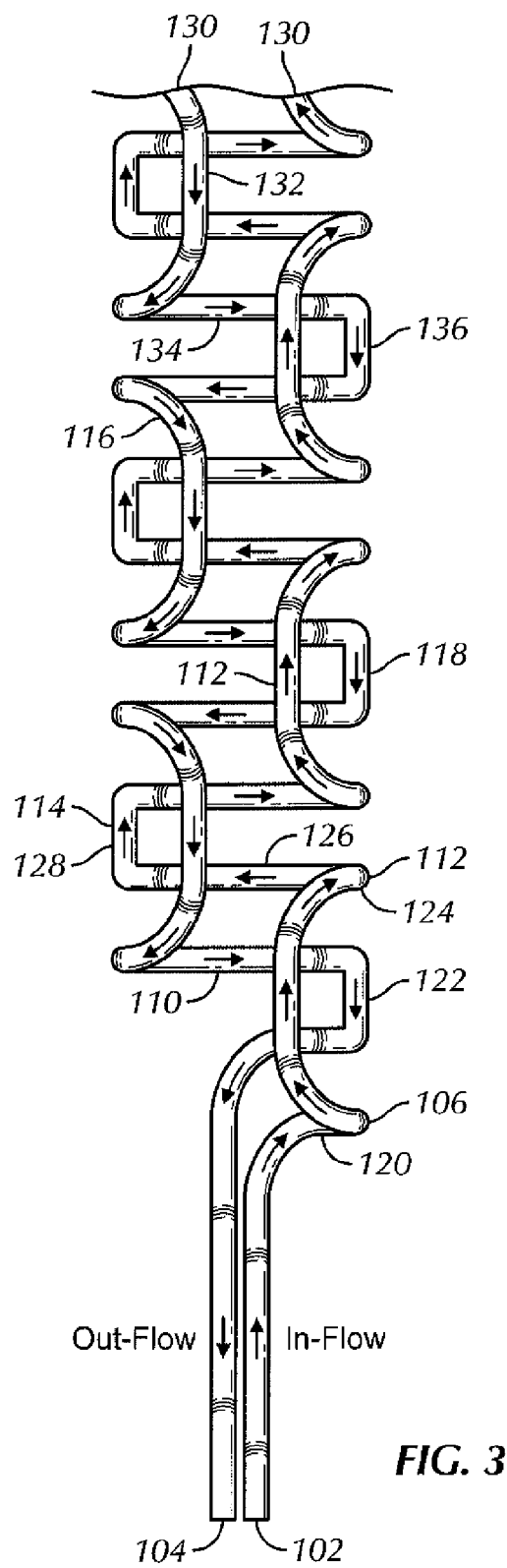
FIG. 3 is a close up view of the heat exchange region.

Now referring to FIGS. 2 and 3, the catheter 10 includes a distal portion 100 which has a supply port 102 configured to communicate with the supply line 16 in FIG. 1 and a return port 104 configured to communicate with the return line 18 in FIG. 1. A heat exchange supply conduit 106 receives working fluid from the supply line 16 and, hence, from a source of working fluid such as the heat exchange system 12. The supply conduit 106 conveys the working fluid to a distal location 108, where it joins a heat exchange return conduit 110 to return working fluid through the return port 104 and thence to the source.

As shown, at least a portion of the supply conduit 106 and/or at least a portion of the return conduit 110 is configured in a serpentine configuration when working fluid flows therethrough. In the example, substantially all of the conduits 106 and 110 are so formed.

Referring particularly to FIG. 3, in the example shown portions 112, 114 of the supply conduit 106 establish axially longer segments and axially shorter segments, respectively. Likewise, portions 116, 118 of the return conduit establish axially longer segments and axially shorter segments, respectively. FIG. 3 shows that axially shorter segments 118 of the return conduit 100 are bordered by and spaced axially between transverse legs of respective axially longer segments 112 of the supply conduit 106. Similarly, axially shorter segments 114 of the supply conduit are bordered by and spaced axially between transverse legs of a respective axially longer segment 116 of the return conduit 110.

As discussed in one example below, when the conduits are inflated with working fluid, a proximal-most transverse segment 120 of the supply conduit ends at a first distally-extending axially-oriented segment 122, which merges at a distal end 124 with a second transverse segment 126, which in turn merges at an opposite end of the second transverse segment 126 with another distally-extending axially-oriented segment 128, and so on. Likewise, when the conduits are inflated with working fluid, a distal-most transverse segment 130 of the return conduit 110 ends at a first proximally-extending axially-oriented segment 132, which merges at a proximal end with a second transverse segment 134, which in turn merges at an opposite end of the second transverse segment with another proximally-extending axially-oriented segment 136, and so on.

In non-limiting examples and as shown in FIG. 3, in each conduit 106, 110, lengths of the axially-oriented segments sequentially alternate between a short length and a long length, while in contrast each transverse segment has substantially the same length as the other transverse segments. Additionally, a long axially-oriented segment of the supply conduit axially spans a short axially-oriented segment of the return conduit, and likewise a long axially-oriented segment of the return conduit axially spans a short axially-oriented segment of the supply conduit. Short axially-oriented segments of the conduits may be substantially straight and parallel to a long axis of the catheter as shown, while long axially-oriented segments (e.g., as shown 112 and 116) of the conduits can be concave.

While the particular INTRAVASCULAR HEAT EXCHANGE CATHETER WITH RIB CAGE-LIKE COOLANT PATH is herein shown and described in detail, it is to be understood that the subject matter which is encompassed by the present invention is limited only by the claims.

What is claimed is:

1. A catheter, comprising:
a supply conduit configured to supply working fluid received from a source to a distal location;
a return conduit communicating with the supply conduit at the distal location and configured to communicate with the source;
wherein the catheter defines a longitudinal axis, and portions of the supply conduit establish axially longer segments and axially shorter segments and wherein portions of the return conduit establish axially longer segments and axially shorter segments, the axially shorter segments being axially shorter segments and the axially longer segments being axially longer segments in that the axially shorter segments are shorter in the dimension defined by the longitudinal axis than the axially loner segments, and further wherein at least one of the axially shorter segments of the return conduit is bordered by and extends axially between first and second transverse segments of at least one of the axially longer segments of the supply conduit, the at least one axially shorter segment of the return conduit extending from the first transverse segment to the second transverse segment, at least one axially shorter segment of the supply conduit being bordered by and axially between first and second transverse segments of at least one of the axially longer segments of the return conduit, the at least one axially shorter segment of the supply conduit extending from the first transverse segment of the at least one of the axially longer segments of the return conduit to the second transverse segment of the at least one of the axially longer segments of the return conduit, at least the axially shorter segments being oriented parallel to the longitudinal axis.

2. The catheter of claim 1, wherein at least when the supply and return conduits are inflated, a proximal-most transverse segment of the supply conduit from among all transverse segments of the supply conduit ends at a first distally-extending axially-oriented segment from among all axially-oriented segments of the catheter, which merges with a second transverse segment from among all the transverse segments, which in turn merges at an opposite end of the second transverse segment with another distally-extending axially-oriented segment from among all axially-oriented segments of the catheter.

3. The catheter of claim 2, wherein at least when the supply and return conduits are inflated, a distal-most transverse segment of the return conduit from among all the transverse segments of the return conduit ends at a first proximally-extending axially-oriented segment from among all the axially-oriented segments of return conduit, which merges via at least one segment of all the segments of the catheter with another proximally-extending axially-oriented segment of all of the axially oriented segments of at least one of the supply or return conduit.

4. The catheter of claim 3, wherein in each the supply and return conduit, the axially shorter segments alternate with the axially longer segments while in contrast each transverse segment does not have a shorter length or long length relative to the other transverse segments.

5. The catheter of claim 4, wherein a first one of the axially longer segments of the supply conduit axially spans a first one of the axially shorter segments of the return conduit, and likewise a first one of the axially longer segments of the return conduit axially spans a first one of the axially shorter segments of the supply conduit.

6. A catheter, comprising:
a heat exchange supply conduit configured to supply working fluid received from a source to a distal location;
a heat exchange return conduit communicating with the supply conduit at the distal location and configured to communicate with the source; wherein
at least a portion of the supply conduit and at least a portion of the return conduit is configured in a configuration when the working fluid flows therethrough, the catheter defining a longitudinal axis, the configuration comprising:
axially longer segments and axially shorter segments, the axially shorter segments being axially shorter segments and the axially longer segments being axially longer segments in that the axially shorter segments are shorter in the dimension defined by the longitudinal axis than the axially longer segments, at least one of the axially shorter segments of the return conduit being bordered by and axially between first and second transverse segments of at least one of the axially longer segments of the supply conduit, the at least one of the axially shorter segments of the return conduit extending from the first transverse segment to the second transverse segment, and at least one of the axially shorter segments of the supply conduit is bordered by and axially between first and second transverse segments of at least one of the axially longer segments of the return conduit, the at least one of the axially shorter segments of the supply conduit extending from the first transverse segment of the at least one of the axially longer segments of the return conduit to the second transverse segment of the at least one of the axially longer segments of the return conduit, at least the axially shorter segments being oriented parallel to the longitudinal axis.

7. The catheter of claim 6, wherein at least when the supply and return conduits are inflated, a proximal-most transverse segment of the supply conduit from among all transverse segments of the supply conduit ends at a first distally-extending axially-oriented segment from among all axially-oriented segments of the catheter, which merges with a second transverse segment from among all the transverse segments, which in turn merges at an opposite end of the second transverse segment with another distally-extending axially-oriented segment from among all axially-oriented segments of the catheter.

8. The catheter of claim 7, wherein at least when the supply and return conduits are inflated, a distal-most transverse segment of the return conduit from among all the transverse segments of the return conduit ends at a first proximally-extending axially-oriented segment from among all the axially-oriented segments of the return conduit, which merges via at least one segment of all the segments of the catheter with another proximally-extending axially-oriented segment of all of the axially oriented segments of at least one of the supply or return conduit.

9. The catheter of claim 8, wherein in each of the supply and return conduit, the axially shorter segments alternate with the axially longer segments while in contrast each transverse segment does not have a shorter length or long length relative to the other transverse segments.

10. The catheter of claim 9, wherein a long axially-oriented segment of the supply conduit axially spans a short axially-oriented segment of the return conduit, and likewise a long axially-oriented segment of the return conduit axially spans a short axially-oriented segment of the supply conduit.

11. The catheter of claim 10, wherein short axially-oriented segments of at least one of the supply or return conduits are parallel to a long axis of the catheter, while long axially-oriented segments of at least one of the supply or return conduits are concave.

12. An intravascular heat exchange catheter defining a longitudinal axis and comprising:
supply and return conduits configured for circulating working fluid with a heat exchange system to warm or cool a patient in which the catheter is intubated, the conduits being in a configuration comprising:
axially longer segments and axially shorter segments, the axially shorter segments being axially shorter segments and the axially longer segments being axially longer segments in that the axially shorter segments are shorter in the dimension defined by the longitudinal axis than the axially longer segments, at least one of the axially shorter segments of the return conduit extending axially from a first transverse segment of at least one of the axially longer segments of the supply conduit to a second transverse segment of the axially longer segment of the supply conduit, and at least one of the axially shorter segments of the supply conduit extends from a first transverse segment of at least one of the axially longer segments of the return conduit to a second transverse segment of the axially longer segment of the return conduit, at least the axially shorter segments being oriented parallel to the longitudinal axis.

13. The catheter of claim 12, wherein at least when the supply and return conduits are inflated, a proximal-most transverse segment of the supply conduit from among all transverse segments of the supply conduit ends at a first distally-extending axially-oriented segment from among all axially-oriented segments of the catheter, which merges with a second transverse segment from among all the transverse segments, which in turn merges at an opposite end of the second transverse segment with another distally-extending axially-oriented segment from among all axially-oriented segments of the catheter.

14. The catheter of claim 13, wherein at least when the supply and return conduits are inflated, a distal-most transverse segment of the return conduit from among all transverse segments of the return conduit ends at a first proximally-extending axially-oriented segment from among all the axially-oriented segments of the return conduit, which merges via at least one segment of all the segments of the catheter with another proximally-extending axially-oriented segment of all of the axially oriented segments of at least one of the supply or return conduit.

15. The catheter of claim 13, wherein in each of the supply and return conduit, the axially shorter segments alternate with the axially longer segments while in contrast each transverse segment does not have a shorter length or long length relative to the other transverse segments.

* * * * *